United States Patent
Steinhoff et al.

(10) Patent No.: US 9,568,446 B2
(45) Date of Patent: Feb. 14, 2017

(54) DEVICE FOR ASCERTAINING THE CORROSIVENESS OF A PLASTIC MELT

(71) Applicant: Fraunhofer-Gesellschaft zur Foerderung der angewandten Forschung e.V., Munich (DE)

(72) Inventors: Bernd Steinhoff, Darmstadt (DE); Dirk Lellinger, Weiterstadt (DE); Hans Kothe, Bischofsheim (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 223 days.

(21) Appl. No.: 14/197,867

(22) Filed: Mar. 5, 2014

(65) Prior Publication Data

US 2014/0253152 A1 Sep. 11, 2014

(30) Foreign Application Priority Data

Mar. 5, 2013 (DE) .................. 10 2013 203 747

(51) Int. Cl.
| | |
|---|---|
| G01N 27/06 | (2006.01) |
| B29C 45/78 | (2006.01) |
| B29C 45/76 | (2006.01) |
| B29C 47/92 | (2006.01) |
| G01N 17/02 | (2006.01) |
| G01N 33/44 | (2006.01) |
| B29C 47/00 | (2006.01) |

(52) U.S. Cl.
CPC .............. *G01N 27/06* (2013.01); *B29C 45/76* (2013.01); *B29C 47/92* (2013.01); *G01N 17/02* (2013.01); *G01N 33/442* (2013.01); *B29C 47/0009* (2013.01); *B29C 2945/76173* (2013.01); *B29C 2945/76454* (2013.01); *B29C 2947/9238* (2013.01); *B29C 2947/92238* (2013.01)

(58) Field of Classification Search
CPC ................................. G01N 27/06; B29C 45/76
See application file for complete search history.

(56) References Cited

U.S. PATENT DOCUMENTS

| | | | | |
|---|---|---|---|---|
| 2,448,676 A | * | 9/1948 | MacMillin | .............. B29C 45/72 219/777 |
| 3,259,840 A | * | 7/1966 | Schaschi | ................ G01N 17/02 324/425 |
| 3,486,996 A | | 12/1969 | Annand | |
| 3,491,012 A | | 1/1970 | Winslow, Jr. | |
| 3,728,058 A | * | 4/1973 | Wheeler | ................ B29C 45/78 425/135 |
| 4,426,618 A | | 1/1984 | Ronchetti et al. | |

(Continued)

*Primary Examiner* — Jermele M Hollington
(74) *Attorney, Agent, or Firm* — Faegre Baker Daniels LLP

(57) ABSTRACT

A device for ascertaining the corrosiveness of a plastic melt, including a housing having a cavity to be filled with plastic melt; a first electrode made of a first material and a second electrode made of a second material, the first electrode and the second electrode each having a contact surface toward the cavity, the standard potential of the first material being higher than that of the second material, and the first electrode and second electrode additionally being connectable to each other via a measuring element for determining an electric current and/or an electric voltage between the contact surfaces.

12 Claims, 3 Drawing Sheets

(56) References Cited

U.S. PATENT DOCUMENTS

| | | | | |
|---|---|---|---|---|
| 4,486,304 A * | 12/1984 | Neuman | | B01D 29/055 |
| | | | | 210/107 |
| 5,271,032 A * | 12/1993 | Phillips | | H05B 3/03 |
| | | | | 373/117 |
| 5,422,061 A * | 6/1995 | Takahashi | | B29C 45/00 |
| | | | | 264/102 |
| 5,523,640 A * | 6/1996 | Sparer | | B29C 35/007 |
| | | | | 165/104.33 |
| 5,948,448 A * | 9/1999 | Schmidt | | B29C 45/281 |
| | | | | 425/192 R |
| 8,740,598 B2 * | 6/2014 | Jenko | | B29C 45/20 |
| | | | | 425/130 |
| 8,911,228 B2 * | 12/2014 | Altonen | | B29C 45/2704 |
| | | | | 425/548 |
| 2003/0137073 A1 * | 7/2003 | Hunold | | B29C 45/0013 |
| | | | | 264/104 |
| 2006/0022362 A1 | 2/2006 | Fish, Jr. et al. | | |
| 2006/0096391 A1 * | 5/2006 | Kappertz | | G01F 1/588 |
| | | | | 73/861.357 |
| 2009/0096120 A1 | 4/2009 | Subramonian et al. | | |
| 2009/0278274 A1 * | 11/2009 | Bader | | B29C 45/7646 |
| | | | | 264/40.6 |
| 2010/0025391 A1 * | 2/2010 | Palombini | | B29C 45/2737 |
| | | | | 219/672 |
| 2012/0291885 A1 * | 11/2012 | Altonen | | B29C 45/77 |
| | | | | 137/487 |
| 2012/0294963 A1 * | 11/2012 | Altonen | | B29C 45/77 |
| | | | | 425/149 |
| 2013/0030723 A1 * | 1/2013 | Gao | | B29C 45/77 |
| | | | | 702/50 |
| 2015/0115491 A1 * | 4/2015 | Altonen | | B29C 45/7646 |
| | | | | 264/40.7 |

* cited by examiner

DEVICE FOR ASCERTAINING THE CORROSIVENESS OF A PLASTIC MELT

CROSS-REFERENCE TO RELATED APPLICATION

This application claims priority to German Patent Application 10 2013 203 747.3, filed Mar. 5, 2013, the disclosure of which is incorporated herein by reference in its entirety.

TECHNICAL FIELD

The present disclosure relates to a device for ascertaining the corrosiveness of a plastic melt. In addition, the disclosure relates to a machine comprising such a device and to a method for measuring the corrosiveness of a plastic melt.

BACKGROUND

Depending on the composition, some polymer plastic materials have highly corrosive properties with respect to iron alloys. These corrosive properties (corrosiveness) can have an adverse effect on parts of plastics processing machines.

The corrosiveness here may be due to flame-retarding additives. These additives can react directly with the iron alloys; however, it is also possible for corrosive chemicals, such as inorganic acids, to develop during or after the thermal decomposition of some additives during production of the plastic melt.

So as to develop a plastic material that not only satisfies maximum requirements in terms of flame proofing, but also does not have a highly corrosive effect on plastics processing machines, an appropriate optimum using a suitable measuring method must be found. The method should supply reproducible results on the one hand, and the amount of material required for measurement should be as small as possible on the other hand.

SUMMARY

It is an object of the present disclosure to describe corresponding devices and machines and methods, which ascertain the corrosiveness of various plastic melts in a cost-effective and simple manner.

This object is achieved by embodiments described in the disclosure. Some embodiments include a device for ascertaining the corrosiveness of a plastic melt, including a housing having a cavity to be filled with plastic melt, a first electrode made of a first material and a second electrode made of a second material, wherein the first and second electrodes each have a contact surface toward the cavity. A standard potential of the first material is higher than that of the second material, and the first and second electrodes additionally can be connected to each other for determining an electric current and/or an electric voltage between the contact surfaces by way of a measuring element.

As a result of the plastic melt present in the cavity, the contact surface of the second electrode is affected by corrosion. The described corrosion process can be metrologically evaluated when the two electrodes are electrically conductively connected by way of an electrically conducting connection and by way of the interposed melt. The consequence of the corrosion process is that electrons flow from the anode (this being the electrode made of the "less noble" material, which is to say having the lower standard potential) to the cathode (this being the electrode made of a material having a higher standard potential). As this corrosion process progresses, a current thus flows, the intensity of which can be ascertained by way of a measuring element used to determine the electric current. This, in turn, is a measure of the corrosiveness.

Taking into consideration the size of the contact surfaces of the electrodes, the absolute value of the current provides information about the corrosion rates, or corrosion speeds, to be expected, which depend on many influencing variables and are difficult to estimate without such a measurement. It is also possible to obtain information about the corrosiveness from the measurement of other electrical variables, such as the potential between the electrodes.

In some embodiments of the device for measuring corrosiveness, additional sensors are installed, preferably temperature sensors, pressure sensors, sensors for optical spectroscopy, ultrasonic measuring technique, dielectric spectroscopy and/or light scattering. All parameters that are relevant for the measurement can thus be standardized.

In some embodiments, the device for measuring the corrosiveness has an opening for feeding plastic melt, for example, for connecting a screw-type extruder. The device described in the disclosure can thus be joined directly to arbitrary devices for producing the plastic melt so as to carry out standardized measurements.

In some embodiments, the cavity that can be filled with plastic melt is elongated and, perpendicularly to the longitudinal direction thereof, has a rectangular, round or oval cross-section, or combinations thereof, at least in some regions. The advantage of this is that these basic geometric shapes allow electrodes having contact surfaces that are as large as possible to be introduced, which are flush with the interior space of the cavity. Moreover, standard geometries also make it easier to clean the cavity.

In some embodiments, the one electrode protrudes, or both electrodes protrude, into the cavity, so that the melt is sheared by the electrode surfaces. The mechanical wear that takes place in the process at the same time allows conclusions of the abrasiveness of the melt.

In some embodiments, the first material is copper, platinum, palladium, amorphous carbon, rhodium, iridium, nickel, silver, gold, iron, or alloys of these, and/or the second material is zinc or an iron alloy, in particular carbon steel.

In some embodiments, the first and/or the second electrode are recessed into the housing as part of an insert. The advantage of this is that the electrodes are easy to replace, such as for cleaning purposes or when they are worn down (in particular the second electrode, this being the electrode having the lower standard potential). The insert can also be designed as a screw insert. The attachment of the insert will thus withstand even maximum pressures, while nonetheless being tight. In addition, the electrode can be "readjusted" in this way, if needed. The electrode is preferably electrically insulated with respect to the housing by way of electrical insulation (such as a ceramic sleeve).

In principle, it is also possible to provide only one electrode as an external insert, and to use a defined portion of the housing as the "other electrode" when a suitable material is used for the housing (which itself is made of carbon steel, for example).

In some embodiments, both electrodes (which is to say the first and second electrodes) are combined in a single insert (electrically insulated with respect to each other).

In some embodiments, the housing can be separated (e.g. divided into two parts) to open the cavity and have better access to the contact surfaces. This not only allows the contact surface to be easily and thoroughly cleaned, but a visual inspection of the surface is also easily possible, such as to draw conclusions of the abrasiveness.

In some embodiments, multiple pairs of first and second electrodes are provided. It is thus possible to carry out various measurements simultaneously. For example, it is possible to provide various materials for the second electrodes, so as to obtain the largest possible number of measured values for a particular plastic melt, using as little plastic material as possible.

Another aspect of the invention relates to a machine, including a device for generating a plastic melt and a device for ascertaining the corrosiveness, as described above. The machines can be an injection molding machine, an extruder or a kneading machine. In some embodiments, the machine has two outlets for plastic melt, wherein a first outlet is connected to the opening of the device for ascertaining the corrosiveness and the second outlet of the machine is not connected to the device for ascertaining the corrosiveness. It is thus possible, to connect an injection mold to the second outlet and continuously produce certain products here. The additional first outlet makes it possible to measure the corrosiveness of the respective material during ongoing operation.

In some embodiments, the first outlet can be closed separately from the second outlet. In this way a measurement can be carried out "at the push of a button", while otherwise being able to operate the machine entirely as usual.

Also, the disclosure relates to a method for measuring the corrosiveness of plastic melts, wherein plastic melt is introduced into a cavity, and a first electrode made of a first material and a second electrode made of a second material are provided, and the first and second electrodes each have a contact surface toward the cavity, wherein the standard potential of the first material is higher than that of the second material, and the first and second electrode can additionally be connected to each other by way of a measuring element, and an electric current and/or an electric voltage between the first and second electrodes can be ascertained.

In some embodiments, less than 1000 g plastic melt is needed when using the method.

BRIEF DESCRIPTION OF THE DRAWINGS

The invention will be described hereafter based on several drawings. In the drawings.

DETAILED DESCRIPTION

Figure 1:
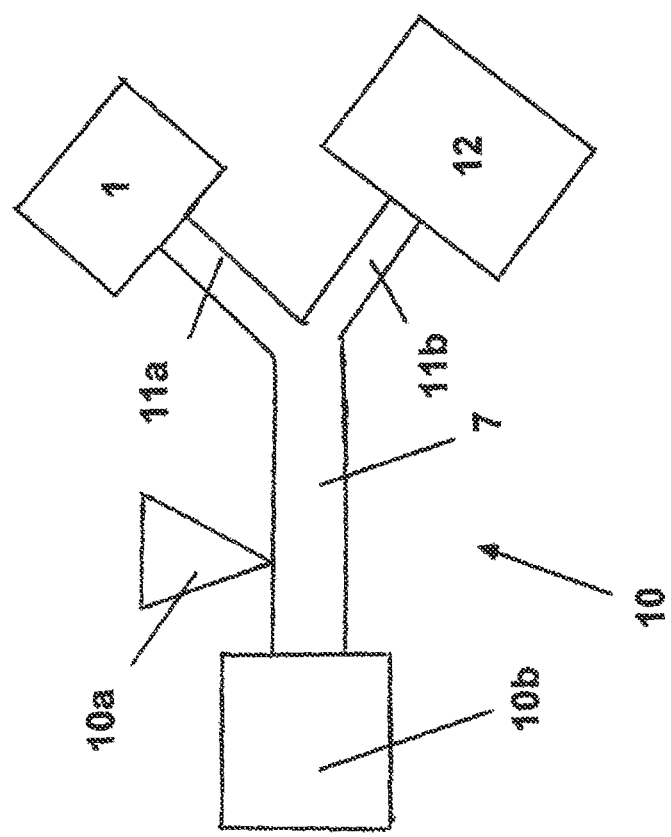
FIG. 1 is a diagram illustrating a machine according to the disclosure including two outlets, wherein the first outlet is connected to a device for ascertaining the corrosiveness, according to some embodiments.

FIG. 1 is a diagram illustrating an injection molding machine, according to some embodiments. This machine includes a device for generating plastic melt 10, which includes a hopper for feeding plastic pellets 10a, a heating device, which is not shown, and a drive system 10b. At the end, a first outlet 11a and a second outlet 11b are provided.

The second outlet 11b can be connected to a plastic injection mold 12, in which plastic vats and the like can be produced. The first outlet 11a is connected to an opening 6 of a device 1 for ascertaining the corrosiveness of a plastic melt.

The outlet 11a can be closed, so that, after this outlet has been closed, only the outlet 11b remains open and a flow of plastic melt to the device 1 is suppressed.

Figure 2A:
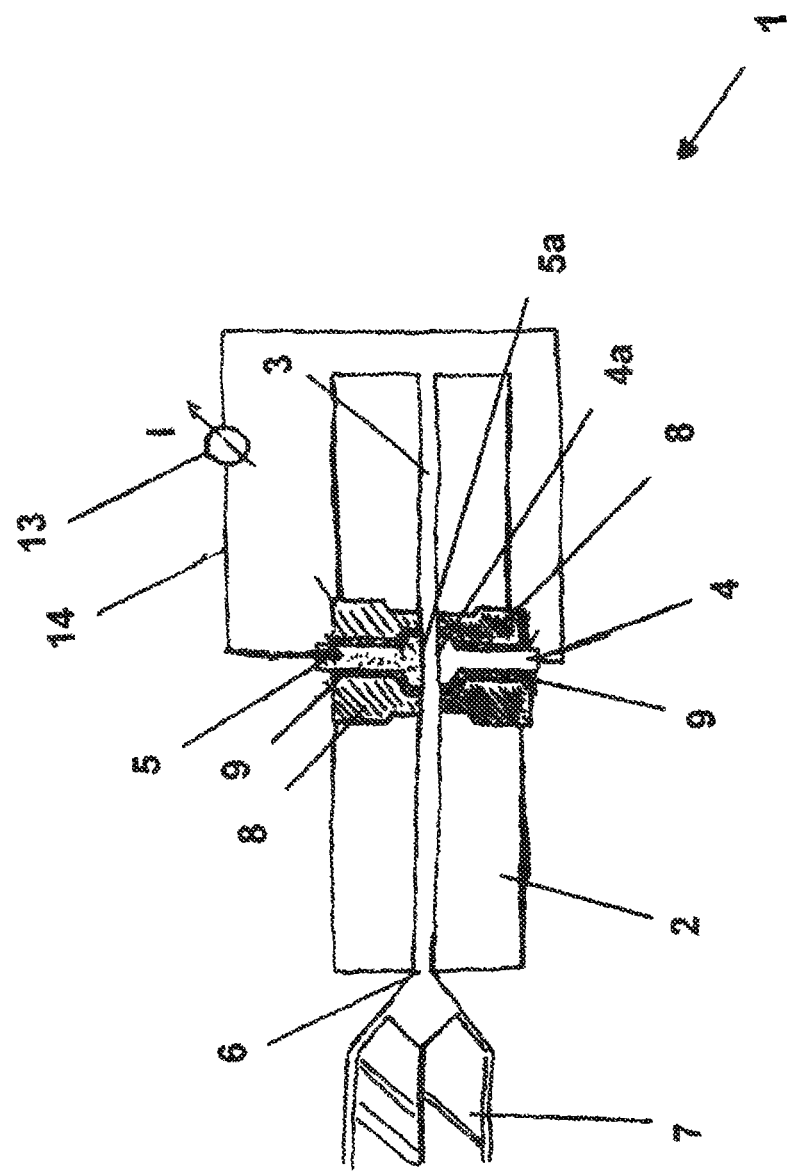
FIG. 2a is a diagram illustrating a cross-section through a device according to the disclosure for measuring the corrosiveness, having a screw-type extruder connected thereto, according to some embodiments.
Figure 2B:
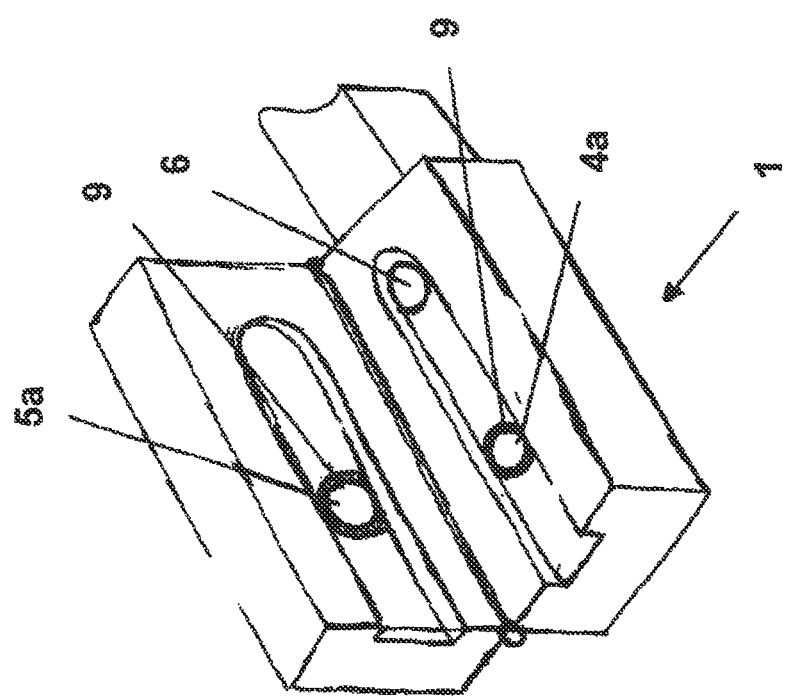
FIG. 2b is a diagram illustrating a device according to the disclosure for ascertaining the corrosiveness, wherein the housing is shown in the open state, according to some embodiments.

Details of the device for ascertaining the corrosiveness of a plastic melt will be addressed hereafter based on FIGS. 2a and 2b.

FIG. 2a is a diagram illustrating a screw-type extruder 7, which is connected to an opening 6 for feeding plastic melt into the device 1 for ascertaining the corrosiveness, according to some embodiments. The device includes a housing 2 having a cavity 3 that can be filled with plastic melt.

The cavity can have a rectangular, round or oval cross-section in the longitudinal direction.

Also shown are two electrodes, these being a first electrode 4 and a second electrode 5. The first electrode 4 is made of a first material, and the second electrode 5 is made of a second material, the standard potential of the first material being higher than that of the second material.

The first electrode has a contact surface 4a toward the cavity, and the second electrode has a contact surface 5a toward the cavity. The electrodes are surrounded by electrical insulation 9 in the form of a ceramic sleeve, which is also part of an insert 8, which can be screwed into the housing 2. At the ends facing away from the cavity, the electrodes are additionally electrically connected to each other by way of an electrical line 14 and a measuring element 13 for measuring electric current.

The contact surface 4a and the contact surface 5a are accommodated essentially flush in the wall of the cavity 3 of the housing 2 of the device 1. In some embodiments, it is advantageous to use, copper, platinum, palladium or alloys of these metals as the first material for the first electrode 4, and to use carbon steel as the second material, this being for the second electrode 5. The device shown in FIG. 2a has only one electrode pair. However, it is also possible to dispose multiple electrode pairs opposite from each other along the length of the cavity 3, so as to be able to carry out multiple measurements at once (for example, using different electrode materials).

FIG. 2b is a diagram illustrating an alternative device 1 in the folded-open state, according to some embodiments. The design regarding the electrodes and the like is identical; the rectangular cross-section of the cavity perpendicularly to the longitudinal direction of the cavity 3 is shown. The location where the plastic melt is fed (see opening 6) should be noted; it is different from FIG. 2a. The device shown in FIG. 2b is divided into two parts, and the cavity 3 can be exposed by folding the housing 2 open, so that the contact surfaces 4a and 5a can be cleaned particularly easily (together with the remaining walls of the cavity), and additionally it is also easily possible to visually inspect the cleaned contact surfaces of the electrodes.

The subject matter shown in FIGS. 1 to 2b is suitable for carrying out a method for measuring the corrosiveness of the plastic melt, wherein plastic melt is introduced into a cavity (3), and a first electrode (4) made of a first material and a second electrode (5) made of a second material are provided, the first and second electrodes each have a contact surface toward the cavity, and wherein the standard potential of the first material is higher than that of the second material, and the first electrode (4) and the second electrode (5) can additionally be connected to each other by way of a measuring element, and an electric current and/or an electric voltage between the first (4) and second (5) electrodes is ascertained by way of a measuring element.

LIST OF REFERENCE NUMERALS 1 device for ascertaining the corrosiveness
2 housing
3 cavity
4 first electrode
4a contact surface of the first electrode
5 second electrode
5a contact surface of the second electrode
6 opening for feeding plastic melt
7 screw-type extruder
8 insert
9 insulation
10 device for generating plastic melt
10a hopper
10b drive system
11a first outlet
11b second outlet
12 plastic injection mold
13 measuring element
14 electrical line

We claim:

1. A device for ascertaining corrosiveness of a plastic melt, comprising:
   a housing having an inlet to receive the plastic melt and a cavity to be filled with the plastic melt such that the plastic melt can flow through the housing as the corrosiveness of the plastic melt is ascertained; and
   a first electrode made of a first material and a second electrode made of a second material, the first electrode and the second electrode each having a contact surface toward the cavity, the standard potential of the first material being higher than that of the second material, and the first electrode and the second electrode additionally being connectable to each other via a measuring element for determining an electric current and/or an electric voltage between the contact surfaces.

2. The device according to claim 1, wherein the inlet of the housing is configured for connecting a screw-type extruder.

3. The device according to claim 1, wherein the cavity is elongated at least in some regions and, perpendicularly to the longitudinal direction of the cavity, has a rectangular, round or oval cross-section, or combinations thereof.

4. The device according to claim 1, wherein the first material is copper, platinum, palladium, amorphous carbon, rhodium, iridium, nickel, silver, gold, iron, or alloys of these, and/or the second material is zinc or an iron alloy or carbon steel.

5. The device according claim 1, wherein the first and/or the second electrodes are recessed into the housing as part of an insert.

6. The device according to claim 5, wherein the insert comprises electrical insulation of the electrode with respect to the housing.

7. The device according to claim 1, wherein the housing can be separated to open the cavity and to have access to the contact surfaces.

8. The device according to claim 1, comprising multiple pairs of first and second electrodes.

9. A machine, comprising:
   a device for generating plastic melt; and
   a device for ascertaining corrosiveness of the plastic melt coupled to the device for generating plastic melt, comprising:
      a housing having an inlet to receive the plastic melt from the device for generating plastic melt and a cavity to be filled with the plastic melt such that the plastic melt can flow through the housing as the corrosiveness of the plastic melt is ascertained; and
      a first electrode made of a first material and a second electrode made of a second material, the first electrode and the second electrode each having a contact surface toward the cavity, the standard potential of the first material being higher than that of the second material, and the first electrode and the second electrode additionally being connectable to each other via a measuring element for determining an electric current and/or an electric voltage between the contact surfaces.

10. The machine according to claim 9, comprising two outlets for the plastic melt, a first outlet connected to the inlet of the device for ascertaining the corrosiveness and the second outlet not being connected to the device for ascertaining the corrosiveness.

11. The machine according to claim 10, characterized in that the first outlet can be closed separately from the second outlet.

12. A method for measuring corrosiveness of plastic melt, comprising:
   introducing the plastic melt into a cavity of a housing having an inlet to receive the plastic melt such that the plastic melt can flow through the housing as the corrosiveness of the plastic melt is ascertained; and
   providing a first electrode made of a first material and a second electrode made of a second material, the first electrode and the second electrode each having a contact surface toward the cavity, the standard potential of the first material being higher than that of the second material, and the first electrode and the second electrode additionally being connectable to each other by way of a measuring element, and an electric current and/or an electric voltage between the first and the second electrodes is ascertained.

* * * * *